US005736479A

United States Patent [19]
Schodel et al.

[11] Patent Number: 5,736,479
[45] Date of Patent: Apr. 7, 1998

[54] OXIDATION CATALYSTS

[75] Inventors: Rainer Schodel, Halle; Peter Birke, Langenbogen; Reinhard Geyer, Halle; Peter Kraak, Leipzig; Willibald Muller; Hans-Dieter Neubauer, both of Merseburg; Rolf Pester, Bad Dürrenberg; Fritz Vogt, Halle; Klaus-Peter Wendlandt, Merseburg, all of Germany

[73] Assignee: Leuna-Katalysatoren GmbH, Leuna, Germany

[21] Appl. No.: 436,409

[22] PCT Filed: Nov. 24, 1993

[86] PCT No.: PCT/DE93/01117

§ 371 Date: May 24, 1995

§ 102(e) Date: May 24, 1995

[87] PCT Pub. No.: WO94/12277

PCT Pub. Date: Jun. 9, 1994

[30] Foreign Application Priority Data

| Dec. 3, 1992 | [DE] | Germany | 42 40 692.7 |
| Dec. 3, 1992 | [DE] | Germany | 42 40 693.5 |
| Dec. 3, 1992 | [DE] | Germany | 42 40 691.9 |
| Dec. 3, 1992 | [DE] | Germany | 42 40 698.6 |

[51] Int. Cl.$^6$ .................................. B01J 29/40
[52] U.S. Cl. .................. 502/77; 502/60; 502/62; 502/63; 502/64; 502/71; 502/73; 502/76; 502/87; 549/531; 564/267; 568/385; 568/311
[58] Field of Search ............. 502/63, 73, 76, 502/77, 87, 60, 62, 64, 71; 549/531; 564/267; 568/385, 311

[56] References Cited

U.S. PATENT DOCUMENTS

| 4,163,756 | 8/1979 | Armor | 260/566 A |
| 4,225,511 | 9/1980 | Armor | 260/566 A |
| 4,281,194 | 7/1981 | Armor et al. | 564/267 |
| 4,410,501 | 10/1983 | Taramasso et al. | 423/326 |
| 4,800,187 | 1/1989 | Lachman et al. | 502/64 |
| 5,214,168 | 5/1993 | Zajacek et al. | 549/531 |
| 5,254,746 | 10/1993 | Costantini et al. | 568/626 |

FOREIGN PATENT DOCUMENTS

| 0100118A1 | 2/1984 | European Pat. Off. |
| 0100119A1 | 2/1984 | European Pat. Off. |
| 0102097A3 | 3/1984 | European Pat. Off. |
| 0102655A2 | 3/1984 | European Pat. Off. |
| 0190609A2 | 8/1986 | European Pat. Off. |
| 0208311A2 | 1/1987 | European Pat. Off. |
| 0226257A2 | 6/1987 | European Pat. Off. |
| 0267362B1 | 5/1988 | European Pat. Off. |
| 0299430B1 | 1/1989 | European Pat. Off. |
| 0311983A2 | 4/1989 | European Pat. Off. |
| 0314582A1 | 5/1989 | European Pat. Off. |
| 0347926A2 | 12/1989 | European Pat. Off. |
| 0469662A1 | 2/1992 | European Pat. Off. |
| 0511739A1 | 11/1992 | European Pat. Off. |
| 3309669A1 | 9/1983 | Germany . |
| 2116974 | 10/1983 | United Kingdom . |

OTHER PUBLICATIONS

Nature –vol. 345 –"Oxyfunctionalization of alkanes with hydrogen peroxide on titanium silicalite" D.R.C. Huybrechts, L. De Bruycker & P.A. Jacobs; May 17, 1990.

Catalysis Letters 13 (1992). Titanium deposited from TiCl$_4$ on amorphous silica and silicalite-1 as catalyst in aromatic hydroxylation reactions, by P.J. Kooyman et al., pp. 229–238.

Journal of Catalysis 131 (1991). Catalytic Properties of Crystalline Titanium Silicalites, by A. Thangaraj et al., pp. 394–400.

Journal of Catalysis 130 (1991). Catalytic Properties of Crystalline Titanium Silicalities, 1. Synthesis and Characterization of Titanium–Rich Zeolites with MFI Structure by A. Thangaru et al., pp. 1–8.

Primary Examiner—Peter O'Sullivan
Attorney, Agent, or Firm—Jordan and Hamburg

[57] ABSTRACT

The invention concerns new oxidation catalysts, methods of producing them and their use. These catalysts consist of titanium silicalites crystallized in situ onto activated charcoal or metal oxides. The titanium silicalite content lies preferably in the range of 30 to 60% by wt. The atomic ratio of Si to Ti in the carrier-borne phase is 10 to 100. Such catalysts are particularly suitable for oxidation reactions with H$_2$O$_2$ under mild conditions, such as temperatures of 20° to 120° C. and pressures equal to or higher than atmospheric.

23 Claims, No Drawings

OXIDATION CATALYSTS

This application is a 371 of PCT/DE93/01117 filed 24 Nov. 1993.

BACKGROUND OF THE INVENTION

The invention relates to new oxidation catalysts, processes for the production thereof as well as the use of these catalysts for oxidation reactions under mild conditions, e.g. temperatures of 20° to 120° C. and pressures equal to or higher than atmospheric pressure.

Numerous oxidation catalysts are already known which are used for oxidation reactions with $H_2O_2$ as an oxidizing agent. In DE-OS 3 309 669, for example, a catalyst is described made of zeolitic materials with foreign elements. Indicated as modifying foreign elements are Cr, Be, Ti, V, Mn, Fe, Ca, Zn, Rh, Ag, Sn, Sb and B.

In recent years, preferably crystalline titanium silicalites have been used as oxidation catalysts. The following applications are known, for example: the synthesis of glycol monomethyl ether (EP 100 118), the epoxidation of mono-olefins (EP 100 119), the epoxidation of di-olefins to monoepoxides (EP 190 609), the conversion of styrene to β-phenylaldehyde (EP 102 097), the hydroxylation of aromatics (GB 2 116 974), the oxidation of alkanes into alcohols and ketones (Nature, 345 (1990) 240), the oxidation of alcohols to aldehydes and ketones respectively (EP 102 655) as well as the conversion of cyclohexanone with $NH_3$ and $H_2O_2$ to the oxime (EP 208 311 and 226 257).

The literature mentions various processes for the production of the crystalline titanium silicalites. In U.S. Pat. No. 4,410,501 two production processes are described. Both processes entail the production of a $TiO_2$—$SiO_2$-gel, which in the presence of tetrapropyl ammonium hydroxide (TPAOH) and water is converted under hydrothermal conditions into the crystalline titanium silicalite (TS-1). As starting products for the gel formation tetraethyl orthosilicate (TEOS) and tetraethyl orthotitanate (TEOT) or colloidal $SiO_2$ and tetrapropyl ammonium peroxotitanate were used. The use of tetrabutyl orthotitanate as a source of $TiO_2$ is described in J. Catal. 130 (1991), 1.

Furthermore, titanium silicalites could be produced by the high temperature treatment of H-ZSM 5 or silicalite-1 with $TiCl_4$ (Catal. Lett. 13 (1992) 229). The EP 299 430 protects a production process of titanium silicalite according to which amorphous $SiO_2$ is impregnated with a titanium compound and then crystallized in the presence of a template to the titanium silicalite.

The hydrothermal conversion of jointly precipitated $TiO_2$—$SiO_2$ products in the presence of templates to titanium silicalite is protected in EP 311 933.

All these titanium silicalite catalysts known from the state of the art have the disadvantage that they are very costly, have a small particle size for batch processes and accordingly are difficult to handle. Furthermore, to ensure high activity and selectivity values an activation with $H_2O_2$ and $H_2SO_4$ is required prior to their use.

SUMMARY OF THE INVENTION

The object of the present invention was, therefore, to develop less costly oxidation catalysts, which in addition also display an improved activity and selectivity behaviour.

This object is achieved by a new catalytic system consisting of titanium silicalite with a MFI-structure crystallized in situ and carried on activated charcoal or on metal oxide.

The titanium silicalite content of the catalysts according to the invention lies within the limits of 1 to 90% by mass; preferably it is 10 to 90% by mass. For titanium silicalite carried on activated charcoal the preferred titanium silicalite content lies in the range of 40 to 60% by mass, whereas for titanium silicalite carried on metal oxide the preferred titanium silicalite content is 30 to 50% by mass.

The Si—Ti atomic ratio in the carried phase is 10 to 100.

As oxides onto which the titanium silicalites are crystallized $Al_2O_3$, $SiO_2$, $TiO_2$, $ZrO_2$ or $Al_2O_3$. $SiO_2$ are used. However, also any mixtures of the indicated oxides can be used.

DETAILED DESCRIPTION OF THE INVENTION

Surprisingly it was found that titanium silicates, applied onto activated charcoal or oxidic carriers, display a considerably improved activity and selectivity compared to the carrier-free titanium silicalites. In addition they also have good sedimentation properties as the particle size of the catalyst measures about $\leq 63$ μm with a maximum in the particle size distribution in the range of 8 to 30 μm. The particle size of the pure titanium silicalites on the other hand measures about $\leq 5$ μm.

The cause of this surprising effect is seen in the interaction which exists between the carrier and the titanium silicalite. Compared to the pure, carrier-free titanium silicalite very different physical-chemical properties occur. These are: a significantly smaller elementary cell volume in the carried titanium silicalite phase as well as a shifting of the Si—O—Ti-bands at 960 $cm^{-1}$ to smaller wave numbers. Significantly smaller means that the reduction lies outside the limit of error of the measurement for pure titanium silicalites.

According to literature data (J. of Catalysis 130, (1991), 1) the elementary cell volume of the titanium silicalite at a Ti/(Ti+Si) atomic ratio of 0 assumes a value of 5.3447 $nm^3$, and in the range of the Ti/(Ti+Si) atomic ratios from 0 to 0.091 increases linearly with the increase in the Ti-content. At a Ti/(Ti+Si) atomic ratio of 0.091 the value of the elementary cell volume is 5.3965 $nm^3$. On the titanium silicalites fixed on the activated charcoal as well as on metal oxide carriers a significant shrinkage of the elementary cells was detected (see Table 1), which is attributed to a structure-influencing effect of the carrier on the zeolitic component.

Table 1 also contains the results of the IR-spectroscopic measurements of titanium silicalites carried on activated charcoal. With the catalysts A, B and C according to the invention, described in the following examples, the band of the Si—O—Ti-oscillation lies between 946 and 949 $cm^{-1}$ and for pure titanium silicalite V as well as the carefully burned-off carrier catalyst A 1 at 967 and 966 $cm^{-1}$, respectively.

The production of the titanium silicalite/activated charcoal carrier catalysts according to the invention can take place according to several processes. Thus it is possible, for example, to apply onto the activated charcoal a $TiO_2$—$SiO_2$-mixture by joint precipitation and to then carry out a hydrothermal treatment, preferably treatment in an autoclave, in the presence of a template, such as tetrapropyl ammonium hydroxide, under autogenous pressure and over a period of 24 to 240 hours at temperatures of 150° to 200° C.

Another production variant consists of the precipitation of $SiO_2$ and activated charcoal and subsequent saturating of the C—$SiO_2$-mixture with a titanium compound, followed by a hydrothermal treatment as indicated above.

Examples at $SiO_2$-sources include for example, water glass and $Si(OC_2H_5)_4$. Suitable titanium compounds are, as is known, $TiOCl_2$ and $Ti(OC_2H_5)_4$.

The production of the titanium silicalite/metal oxide carrier catalysts can take place by the joint precipitation of a $TiO_2$—$SiO_2$-mixture in thee presence of tetrapropyl ammonium hydroxide over a period of 48 to 240 hours at temperatures of 150° to 200° C.

Another production variant is the precipitation of $SiO_2$ onto the carrier with subsequent saturation of the carrier/$SiO_2$ mixture with a titanium compound followed by a hydrothermal treatment in the presence of a template. This is followed by washing, filtering and tempering according to standard procedures.

A third possibility is the impregnating of the metal oxide with a titanium containing silica sol followed by a hydrothermal treatment.

As a $TiO_2$-source it is also possible to use $TiOCl_2$ and $Ti(OC_2H_5)_4$ and as a Si-source water glass and $Si(OC_2H_5)_4$.

A further object of the invention is the use of the catalysts according to the invention for oxidation reactions under mild conditions, such as temperatures from 20° to 120° C. and pressures equal to or higher than atmospheric pressure, and using $H_2O_2$.

Further application possibilities for the catalysts according to the invention exist also in the following reactions with improved effectiveness:

Hydroxylation of aromats

Oxidation of saturated hydrocarbons

Oxidation of olefins

Oxidation of allyl alcohol

Oxidation of alcohols, preferably to aldehydes

These catalysts are particularly preferred for the production of oximes by catalytic conversion of the corresponding carbonyl compound.

As a matter of fact, surprisingly it was found that these carrier catalysts, during the conversion of ketones with $NH_3$ and $H_2O_2$, also without prior activation with $H_2O_2$ and $H_2SO_4$, display a clearly higher activity than pure titanium silicalite catalysts (see Table 2).

The performing of the process for the production of oximes by conversion of the corresponding carbonyl compound with ammonia and $H_2O_2$, when using the catalyst according to the invention carried on activated charcoal, takes place at $H_2O_2$:carbonyl compound molar ratios of 0.8 to 1.2, $NH_3$:carbonyl compound molar ratios of 1.2 to 2.5, temperatures of 20° to 120° C., a pressure equal to or higher than atmospheric pressure, in water and an organic solvent, whilst stirring briskly.

If a catalyst according to the invention carried on metal oxide is used for this, then $H_2O_2$:carbonyl compound molar ratios of 0.8 to 2.0 are used.

When performing this process first the catalyst, the solvent and ammonia are put in and $H_2O_2$ as well as the carbonyl compound are fed in simultaneously but separately by dosing devices, wherein the dosing speeds for $H_2O_2$ and carbonyl compound may not exceed 0.5 mole and 0,4 mole respectively per kg of catalyst per hour. High oxime yields are obtained when the catalyst concentration for the titanium silicalites carried on activated charcoal lies in the range of 0.02 to 30 g per mole of carbonyl compound. Catalyst concentrations of 1 to 6 g of catalyst per mole of carbonyl compound have proved particularly favourable. For the titanium silicalites carried on metal oxide the catalyst concentrations should lie in the range of 0.05 to 30 g, preferably 1 to 8 g, per mole of carbonyl compound.

Furthermore, to achieve high selectivities and activities, reaction temperatures of 60° to 90° C. and low overpressures of 200 to 700 Torr are favourable.

This high ammoximation or oxidation activity is attributed—as already mentioned—to a distortion of the zeolite lattice associated with the interaction between the titanium silicalite and the carrier.

When using the catalysts according to the invention for the above-mentioned reactions, it is important that the titanium silicalite content in the carrier catalyst amounts to 1 to 90% by mass, expediently 10 to 90% by mass, and preferably 40 to 60% by mass when using activated charcoal as the carrier material, and 30 to 50% by mass when using metal oxide as the carrier material, and that the Si/Ti atomic ratio lies in the range of 10 to 100.

The size of the catalyst particles lies under 63 μm. For performing the mentioned processes under industrial conditions, a catalyst particle size spectrum in the range of 8 to 30 μm has proved particularly favourable.

The catalysts produced according to the following examples 1 to 4 were made according to the methods a, b and c. The catalysts produced according to the examples 5 to 9 were made according to the methods b and c:

a) IR-spectroscopy to determine the position of the Si—O—Ti oscillation band. (KBr—pressing method)

b) Radiographic determination of the elementary cell volume (ECV) of the activated charcoal carried titanium silicalite.

The calculation of the elementary cell volume of the zeolitic component takes place from the radiographic precision measurement of the five intensity-strong interferences (501), (051), (151), (303) and (133) in the angle range $2\upsilon=23.0$ to $2\upsilon=25.8$ with Ni-filtered Cu-Kα-radiation on a horizontal metering cube goniometer HZG 4/B of Freiberger Präzisionsmechanik GmbH (recording conditions: step size $\Delta 2\upsilon=\frac{1}{100}°$, measuring time/measuring point t=60 sec., divergence diaphragm $b_{div}=1.09$ mm; metering tube diaphragm $b_z=0.13$ mm). To ensure a specific water content, prior to the test the sample is placed for at least 12 h above a saturated $MgCl_2$-solution.

The line positions are determined and made absolute by an internal standard (corundum) by means of a peak-search programme. The computer programme used for calculating the elementary cell volume is based on a monoclinal lattice symmetry into which the orthorhombic system of the titanium silicalite with MFI-structure fits in as a special case. (MFI: IUPAC-name for calcined ZSM 5-zeolite).

c) Determination of the catalytic activity in the conversion of cyclohexanon with ammonia and $H_2O_2$ to cyclohexanonoxime.

Table 1 shows the elementary cell volumes for a pure titanium silicalite as comparison catalyst V, for the titanium silicate/activated charcoal carrier catalysts A to C, for a carrier free titanium silicalite which was obtained by a 20-hour burning off of the carbon from the catalyst A according to the invention at 500° to 550° C., and for the catalysts D to J carried on metal oxide. During the synthesis of the catalysts according to the invention mentioned in Table 1, a Ti/(Ti+Si)-value of 0.06 was used.

The data in the table show that the elementary cell of the carried titanium silicalite is subject to a great shrinkage. After a careful burning off of the activated charcoal the elementary cell volume is again the same as that of pure titanium silicalite.

The structure-influencing effect of the carrier on the zeolitic component is also shown by the results of the IR-spectroscopic measurements. With the catalysts A, B and C according to the invention the band of the Si—O—Ti-oscillation lies at 947, 946 and 949 cm$^{-1}$ respectively, and with the pure titanium silicalite (catalyst V) as well as the carefully burned off carrier catalyst A 1 it is 967 and 966 cm$^{-1}$ respectively.

In Table 2 the catalytic activities and selectivities of the catalysts according to the invention are summarized. The results show their advantages, in particular with regard to the high oxime yield at a high selectivity.

Further advantages include the following:

these catalysts do not require a prior activation with $H_2O_2$ and $H_2SO_4$, the catalyst consumption is lower, less by-products occur, and a smaller amount of costly titanium silicalites is required.

It was furthermore found that the carried titanium silicalites are easier to handle due to the size of the particles of ≦63 μm with a maximum of the particle size distribution in the range of 8 to 30 μm.

EXAMPLE 1 (COMPARISON EXAMPLE)

To 54.4 g of tetraethyl orthosilicate, whilst scavenging with nitrogen and stirring, 2.4 g of tetraisopropyltitanate were added. This mixture was then mixed drop by drop with 120 g of tetrapropyl ammonium hydroxide solution (20%). The mixture was left for one hour at room temperature and then slowly heated to 78° C., kept at this temperature for one hour and then heated to 98° C. to remove the isopropanol. After cooling, the volume of the liquid was topped up to 200 ml with distilled water. The obtained product was treated in an autoclave at 175° C. and under autogenous pressure for a period of 10 days. Next the reaction product was cooled to room temperature, filtered, washed to pH=7, dried for 15 h at 120° C. and then calcined for 10 h at 420° C. Then the catalyst was treated at 70° C. for two hours with a mixture of 10 cm$^3$ $H_2O_2$ (30% by mass) and 100 ml $H_2SO_4$ (5% by mass), whilst stirring.

Next the liquid was separated by decanting and the $H_2O_2$—$H_2SO_4$ treatment was repeated another two times. The crystalline product was then washed to pH 7, dried for 15 h at 120° C. and then heat-treated for two hours at 550° C.

The obtained product is indicated in Table 2 as catalyst V (particle size≦5 μm).

EXAMPLE 2

To 78.66 g of tetraethyl orthosilicate, whilst scavenging with inert gas and stirring, 2.21 g of tetraethylorthotitanate are added. Then, also whilst scavenging with inert gas, 172.5 g of 20% tetrapropyl ammonium hydroxide solution are added. This mixture is treated for one hour at 78° C. whilst stirring and diluted with 157.32 g of water. Fed into this solution are 15 g of acid washed activated charcoal from spruce wood (DARCO, particle size<32 μm). The homogeneous suspension is transferred at room temperature into a teflon coated autoclave, which in the course of 90 minutes is heated to 175° C. The reaction mixture is left for 120 h at this temperature and under autogenous pressure and whilst stirring. After cooling to room temperature and opening the autoclave, the crystallised product is separated from the mother lye on a frit, washed several times with distilled water and then air dried at 120° C. for 6 h. Next, the catalyst is heated to 550° C. in an inert gas flow (10 l/h) at a heating-up speed of 10° C./minute and left at this temperature for 4 h and subsequently cooled to room temperature in the nitrogen flow.

The obtained product is called catalyst A.

EXAMPLE 3

The same as example 2, but with this example instead of 15 g of activated charcoal, 20.7 g of activated charcoal are added. The obtained product is called catalyst B.

EXAMPLE 4

86.5 ml of waterglass (347 g of $SiO_2$/l) are dissolved in 500 ml $H_2O$. To this solution 30 g A-charcoal (DARCO, particle size≦32 μm) are added. The obtained suspension is stirred for 30 minutes at room temperature.

Next, within 30 minutes the mixture is precipitated with diluted $H_2SO_4$ (3.8% by mass) up to the pH-value 5.8. The obtained precipitate suspension is stirred for a further 30 minutes at room temperature. The $SiO_2$ precipitated on activated charcoal is filtered, washed and air dried for 24 h at 80° C.

Next, 8.84 g of tetraethyl orthotitanate are dissolved in 400 ml ethanol under inert gas conditions. The produced activated charcoal/$SiO_2$ product is added to this clear solution. The resultant suspension is treated in a vacuum rotation evaporator under a vacuum of 16 mbar up to dryness of the carrier. The saturated carrier is suspended in 690 g of 20% tetrapropyl ammonium hydroxide solution and 640 g water and transferred to an autoclave, heated to 175° C. in the course of 90 minutes, and left at this temperature for 120 h. After cooling to room temperature and opening the autoclave, the product is separated from the mother lye on a filter and washed several times with water. Next, the product is air dried over a period of 6 h at 120° C. and then heated to 550° C. in a nitrogen flow at a heating-up speed of 10° C./minute, left at this temperature for 4 h and then cooled to room temperature whilst scavenging with nitrogen. The obtained catalyst is listed in Table 2 under the name catalyst C.

EXAMPLE 5

2.21 g of tetraethyl orthotitanate are added, whilst stirring and scavenging with inert gas, to 78.66 g of tetraethyl orthosilicate. Then, also whilst scavenging with inert gas, 172.5 g of 20% by mass tetrapropyl ammonium hydroxide solution are added. This mixture is treated for one hour at 78° C. whilst stirring and diluted with 157.32 g of water. Fed into this solution are 15 g of $SiO_2$ (surface: 385 m$^2$/g, particle size<32 μm). The homogeneous suspension is transferred at room temperature into a teflon coated autoclave and heated within minutes to 175° C. The reaction mixture is left at this temperature under autogenous pressure. After cooling to room temperature and opening the autoclave, the crystallised product is separated from the mother lye on a filter, washed several times with distilled water and then air dried at 120° C. Next, the dried product is heated to 550° C. in an air flow (10 l/h) at a heating-up speed of 10° C./min. and left at this temperature for 2 h. Next the catalyst is cooled to room temperature.

The obtained product is called catalyst D.

EXAMPLE 6

The same as example 5, but instead of $SiO_2$, 15 g of $Al_2O_3.SiO_2$ (20% by mass $SiO_2$, 226 m$^2$/g, particle size≦32 μm) are used as the carrier. The catalyst is referred to in Tables 1 and 2 as catalyst E.

EXAMPLE 7

The same as example 5, but instead of $SiO_2$, 17 g of $ZrO_2$ (15.6 m²/g, particle size≦32 μm) are used as carrier.

The catalyst is referred to in Tables 1 and 2 as catalyst F.

EXAMPLE 8

21.6 ml of waterglass with an $SiO_2$-content of 347 g/l are dissolved in 125 ml of water. To this solution 7.5 g γ-$Al_2O_3$ (186 m²/g, particle size≦32 μm) are added. This suspension is stirred for 20 minutes at room temperature and then within a period of 20 minutes precipitated with diluted $H_2SO_4$ (3.8% by mass) up to the pH-value of 5.9. Next, the suspension is stirred for a further 30 minutes at room temperature. The $SiO_2$ precipitated on $Al_2O_3$ is filtered, washed and air dried for 6 h at 120° C. Then 2.21 g of tetraethyl orthotitanate are dissolved quickly in 100 ml ethanol whilst scavenging with inert gas. The produced $Al_2O_3/SiO_2$ product is added to this solution. The resultant suspension is treated in a vacuum reaction evaporator under a vacuum of about 16 mbar up to dryness of the solid substance mixture. The mixture is suspended in 172.5 g of 20% by mass tetrapropyl ammonium hydroxide solution and 160 g water and transferred to a teflon coated autoclave. This suspension is heated to 178° C. within 90 minutes, and left at this temperature for 120 h. After cooling to room temperature and opening the autoclave, the product is separated from the mother lye by filtration and washed several times with water. Next, the product is air dried over a period of 6 h at 120° C. and then heated in air to 550° C. at a heating-up speed of 10° C./minute, left at this temperature for 3 h and then cooled to room temperature. The obtained catalyst is called catalyst G.

EXAMPLE 9

The same as example 8, but instead of $Al_2O_3$, 16 g of $TiO_2$ (21.0 m²/g, particle size≦32 μm) are used as the carrier. The formed product is catalyst H.

EXAMPLE 10

The same as example 8, but instead of $Al_2O_3$, a mixture of 5 g of $ZrO_2$, 4 g of γ-$Al_2O_3$ and 6 g of $SiO_2$ are used to produce the catalyst. The obtained product is indicated in Table 2 as catalyst J.

EXAMPLE 11

The determination of the catalytic activity of the catalysts according to the invention as well as of the comparison catalyst takes place by using them in the conversion of cyclohexanone with ammonia and $H_2O_2$ to cyclohexanonoxime.

To this end, in each instance, 1.0 g of catalyst, 48 ml of $NH_3/H_2O$ (13.8% by mass) and 42 ml of t-butanol are put in a reaction vessel. This suspension is heated to 80° C. whilst stirring briskly. After reaching the reaction temperature, by means of two dosing devices, 19 g of $H_2O_2$ (30%) and 17 g cyclohexanone added to the suspension over a period of 270 minutes, whilst stirring. Next, the reaction mixture is kept for a further 30 minutes at reaction temperature and then cooled to room temperature. During the reaction, at the beginning an overpressure of 630 to 760 Torr occurs, which at the end of the reaction drops to a value of about 300 Torr.

To process the reaction mixture, the catalyst is centrifuged off and the liquid product is mixed with 20 ml cyclohexane, which was previously used to rinse the apparatus, and 20 g ammonium sulphate. After a five minute extraction the phases are separated, and the aqueous phase is extracted another five times with, in each instance, 10 ml cyclohexane. The organic extracts are combined and analysed by gas-chromatography. The results of the test are contained in Table 2.

EXAMPLE 12

In an autoclave scavenged with nitrogen (200 ml capacity) 7.4 g of n-hexane, 17.8 g of acetone, 17.5 g of $H_2O_2$ (35%) are mixed with 0.25 g of the catalyst V and 0.3 g of the catalyst H respectively (corresponds to a zeolite content of 0.15 g). The reaction mixture is converted for 60 min at 95° C. whilst stirring (600 revolutions/min), and then, after cooling to room temperature, analysed. As a result, the n-hexane is converted to 1-hexanol, 2-hexanol, 2-hexanone and 3-hexanone. The n-hexane conversion with the catalyst V is 54% and with the catalyst H according to the invention 63%.

EXAMPLE 13

48 g of 1-heptanol, 80 g of acetone and 6.5 g of the catalyst V and 12 g of the catalyst E according to the invention (corresponds to a zeolite content of 5.8 g), respectively, are fed into a reaction vessel fitted with a reflux cooler, heated to 65° C., then mixed within 30 min. with 10 g of $H_2O_2$ (35%) and then treated for 5 h whilst stirring. After cooling to room temperature the reaction mixture is analysed. The percentage of heptanol converted to heptanal was 14.5% with catalyst V and 16.8% with catalyst E of the invention.

EXAMPLE 14

12 g of allyl alcohol, 30 g of tert.-butyl alcohol, 100 g of water, 22 g of $H_2O_2$ (35%) together with 3.5 g of the catalyst V and 6.9 g of the catalyst E according to the invention (corresponds to 3.4 g zeolite content), respectively, are fed into a reaction vessel and stirred for 8 h at 30° C. Then the reaction mixture was analysed. With the catalyst V a glycerine yield of 78.2%, related to the used allyl alcohol, and with the catalyst E according to the invention a glycerine yield of 83.7% was measured.

EXAMPLE 15

47 g of phenol, 10 g of water, 25 g of acetone, 16.3 g of $H_2O_2$ (35%) and 4.5 g of the catalyst V and 7 g of the catalyst G according to the invention (corresponds to 3.4 g zeolite content), respectively, are fed into a reaction vessel fitted with a reflux cooler and stirred for 5 h at 60° C. Then the reaction mixture is cooled and analysed. The analysis showed a phenol conversion of 28.9% for the catalyst V and 30.9% for the catalyst G according to the invention. The reaction product composition was, in both cases, 48% hydroquinone and 52% catechol.

EXAMPLE 16

10 g of 1-octene and 40 g of methanol together with 4.5 g catalyst V, or 6 g catalyst F (corresponds to a zeolite content of 2.9 g), or 6.4 g catalyst J (corresponds to a zeolite content of 3.2 g), respectively, are put into a reaction vessel and heated to 48° C. Then, in each instance, 5 g of $H_2O_2$ (35%) are added drop by drop whilst stirring. After 90 minutes reaction time, the reaction mixture is cooled and analysed. The following results were obtained:

| Catalyst | 1-octene conversion | Selectivity of the 1,2-epoxide formation |
|---|---|---|
| V | 50,1% | 92,5% |
| F | 54,4% | 93,4% |
| J | 55,9% | 93,5% |

The examples 12 to 16 illustrate that the oxidation activity of the carried titanium silicalites, related to the zeolite content, is greater than that of the carrier-free zeolite phase.

TABLE 1

| Catalyst | ECV in nm$^3$ | Position of the IR-band (Si—O—Ti) in cm$^{-3}$ |
|---|---|---|
| V | 5,3794 | 967 |
| A | 5,3390 | 947 |
| B | 5,3379 | 946 |
| C | 5,3501 | 949 |
| A 1 1) | 5,3744 | 966 |
| D | 5,3632 | n.d. |
| E | 5,3594 | n.d. |
| F | 5,3580 | n.d. |
| G | 5,3619 | n.d. |
| H | 5,3625 | n.d. | n.d. = not determined
1) A 1 was obtained from the catalyst A by a 20-hour careful burning off of the carbon at temperatures of 500 to 550° C.

TABLE 2

| Catalyst | Oxime yield in % | Selectivity* in % |
|---|---|---|
| V | 88,7 | 94,6 |
| A | 92,8 | 98,4 |
| B | 91,3 | 98,1 |
| C | 91,0 | 98,3 |
| D | 92,4 | 98,1 |
| E | 90,9 | 98,0 |
| F | 91,4 | 98,3 |
| G | 92,1 | 98,1 |
| H | 92,2 | 97,9 |
| J | 91,7 | 98,5 |

*related to the cyclohexanone conversion

We claim:

1. An oxidation catalyst consisting of titanium silicalite with a MFI-structure crystallized in situ and carried on metal oxide selected from the group consisting of Al$_2$O$_3$, SiO$_2$, TiO$_2$, ZrO$_2$, Al$_2$O$_3$.SiO$_2$ and mixtures of these oxides, the oxidation catalyst having a titanium silicalite content of 1 to 90% by mass and a Si:Ti atomic ratio in the carried phase of 10 to 100.

2. An oxidation catalyst according to claim 1 with a titanium silicalite content of 10 to 90% by mass.

3. An oxidation catalyst according to claims 1 with an elementary cell volume of the carried titanium silicalite phase significantly smaller than that of a corresponding carrier-free titanium silicalite.

4. A process for the production of an oxidation catalyst according to claim 1 comprising precipitating a TiO$_2$/SiO$_2$ mixture onto metal oxide; treating in an autoclave in the presence of a template under autogenous pressure at temperatures of 150° to 200° C. over a period of 48 to 240 hours; washing; filtering and tempering.

5. A process for the production of an oxidation catalyst according to claim 1 comprising precipitating SiO$_2$ onto metal oxide and saturating with a titanium compound; treating in an autoclave in the presence of a template under autogenous pressure at temperatures of 150° to 200° C. over a period of 48 to 240 hours; washing; filtering and tempering.

6. An oxidation catalyst according to claim 1 with a titanium silicalite content of 40 to 60% by mass.

7. An oxidation catalyst consisting of titanium silicalite with a MFI-structure crystallized in situ and carried on activated charcoal, with a titanium silicalite content of 40 to 60% by mass.

8. An oxidation catalyst according to claim 7 with an elementary cell volume of the carried titanium silicalite phase significantly smaller than that of a corresponding carrier-free titanium silicalite.

9. An oxidation catalyst according claim 1, with a titanium silicalite content of 30 to 50% by mass.

10. An oxidation catalyst according to claim 7 with a Si:Ti atomic ratio in the carried phase of 10 to 100.

11. A process for the production of an oxidation catalyst comprising
precipitating a TiO$_2$/SiO$_2$ mixture onto activated charcoal
and treating in an autoclave in the presence of a template under autogenous pressure at temperatures of 150° to 200° C. over a period of 24 to 240 hours, the resulting oxidation catalyst consisting of titanium silicalite with a MFI-structure crystallized in situ and being carried on activated charcoal.

12. The process of claim 11 wherein the oxidation catalyst has a titanium silicalite content of 1 to 90% by mass.

13. The process according to claim 11 wherein the oxidation catalyst has a titanium silicalite content of 10 to 90% by mass.

14. The process according to claim 11 wherein the oxidation catalyst has a Si:Ti atomic ratio in the carried phase of 10 to 100.

15. The process according to claim 11 wherein the oxidation catalyst has an elementary cell volume of the carried titanium silicalite phase significantly smaller than that of a corresponding carrier-free titanium silicalite.

16. The process according to claim 11 wherein the oxidation catalyst has a titanium silicalite content of 40 to 60% by mass.

17. A process for the production of an oxidation catalyst according to claim 1 comprising
saturating a metal oxide with a titanium containing silica sol;
treating in an autoclave in the presence of a template under autogenous pressure at temperatures of 150° to 200° C. over a period of 48 to 240 hours; washing; filtering and tempering.

18. A process for the production of an oxidation catalyst comprising precipitating SiO$_2$ onto activated charcoal and saturating with a titanium compound; and treating in an autoclave in the presence of a template under autogenous pressure at temperatures of 150° to 200° C. over a period of 24 to 240 hours, the resulting oxidation catalyst consisting of titanium silicalite with a MFI-structure crystallized in situ and being carried on activated charcoal.

19. The process of claim 18 wherein the oxidation catalyst has a titanium silicalite content of 1 to 90% by mass.

20. The process of claim 18 wherein the oxidation catalyst has a titanium silicalite content of 10 to 90% by mass.

21. The process of claim 18 wherein the oxidation catalyst has a Si:Ti atomic ratio in the carried phase of 10 to 100.

22. The process of claim 18 wherein the oxidation catalyst has an elementary cell volume of the carried titanium silicalite phase significantly smaller than that of a corresponding carrier-free titanium silicalite.

23. The process according to claim 18 wherein the oxidation catalyst has a titanium silicalite content of 40 to 60% by mass.

* * * * *